(12) United States Patent
Dicks

(10) Patent No.: US 6,524,631 B1
(45) Date of Patent: Feb. 25, 2003

(54) BAKING MIXES WHICH CONTAIN FLOUR AND HAVE AN ENHANCED SHELF LIFE AND METHOD AND MEANS FOR PREPARING SAME

(75) Inventor: Leon Milner Theodore Dicks, Western Cape Province (ZA)

(73) Assignee: Goodbuy to Dry International LLC, Douglas (GB)

( * ) Notice: Subject to any disclaimer, the term of this patent is extended or adjusted under 35 U.S.C. 154(b) by 0 days.

(21) Appl. No.: 09/937,301

(22) PCT Filed: Mar. 30, 2000

(86) PCT No.: PCT/ZA00/00063

§ 371 (c)(1),
(2), (4) Date: Sep. 25, 2001

(87) PCT Pub. No.: WO00/59308

PCT Pub. Date: Oct. 12, 2000

(30) Foreign Application Priority Data

Apr. 2, 1999 (ZA) .............................. 99/1654

(51) Int. Cl.⁷ ................................. A21D 8/04
(52) U.S. Cl. .................... 426/18; 426/335; 426/552
(58) Field of Search .................... 435/139, 252.9; 426/335, 18, 552, 654, 555, 442, 496

(56) References Cited

U.S. PATENT DOCUMENTS 3,963,835 A    6/1976    Gryczka ................... 426/18

FOREIGN PATENT DOCUMENTS

WO        9613981        5/1996

OTHER PUBLICATIONS

Olukoya, Tichaczek, Butsch, Vogel, Hammes "Characterisation of the bacteriocins produced by Lactobacillus Pentosus DK7 isolated from ogi and Lactobacillus plantarum dk9 from fufu", Chemie Mikrobiologie, Technologie Der Lebensmittel, vol. 15, No. 3/4, pp. 65–68 (1993).

Van Reenen, Dicks "Evaluation of numericla analysis of Random amplified polymorphism DNA (rapd)–pcr as a method to differentiate Lactobacillus plantarum and Lactobacillus pentosus", Current Microbiology, vol. 32, No. 4, pp. 183–187 (1996).

*Primary Examiner*—Keith Hendricks
(74) *Attorney, Agent, or Firm*—Stevens, Davis, Miller & Mosher, LLP

(57) ABSTRACT

A method of preparing a shelf life enhancing composition for baking mixes which contain flour with particular application to batter mixes is provided as well as a microbiological species (*Lactobacillus plantarum/pentosus*) used in the method. The method comprises forming a starting mixture including flour and water and inoculating same with a culture of the LPP strain micro-organisms; allowing the mixture to ferment in order to produce anti-microbial substances including lactic acid, a peptide and possibly other presently unidentified anti-microbial substances; and terminating the fermentation process and destroying all living cells prior to the pH of the mix decreasing to 3.3 to yield a shelf life enhancing composition. Baking mixes embodying the shelf life enhancing composition are also described.

20 Claims, No Drawings

BAKING MIXES WHICH CONTAIN FLOUR AND HAVE AN ENHANCED SHELF LIFE AND METHOD AND MEANS FOR PREPARING SAME

FIELD OF THE INVENTION

This invention relates to baking mixes which contain flour and have an enhanced shelf life and to a method and means for preparing same, More particularly the invention is concerned with the inhibition of spoilage bacteria in such mixes using a substantially naturally produced composition.

Although the invention relates in general to the enhancement of the shelf life of baking mixes which contain flour, it has particular application to confectionery pre-bakes and especially to muffin batter. Such batters generally comprise a mixture of flour and beaten egg, typically with milk or water added. They are generally placed in a suitable shaped container and exposed to heat for cooking, usually referred to as baking.

FIELD OF THE INVENTION

In many catering applications, between a baking mix preparation stage and the eventual cooking stage, there is often a lengthy delay. This results from the practicalities of the food industry in which batch processes for the preparation of baking mixes are generally followed if not by reason of practical necessity then at least for reasons of convenience. Also, economies of scale favour the preparation of larger batches rather than smaller ones and in consequence a mix may be required to stand or be stored before ultimate use. In this precooking delay, spoilage producing micro-organisms and harmful pathogens tend to develop, often leading to a rather limited shelf life.

Conventional batter preservation methods aim at "immobilizing" spoilage producing microbial species present in constituents added to a mix, freezing being one of the most common of these. Lengthy periods of freezing are however known to cause deleterious effects in such mixes, such as an adverse effect on the physical structure of the crystals and other properties determining the texture of the baked product. Irrespective of this, the transport and storage of frozen mixes is costly and requires considerable storage space. Other shelf life enhancing synthetic substances have been proposed and are available on the market but are not, as far as applicant is aware, popular for a number of different reasons not least of which is the general tendency away from synthetic substances.

OBJECT OF THE INVENTION

It is an object of the present invention to provide a substantially natural method and means for inhibiting the growth of spoilage bacteria in baking mixes which contain flour.

SUMMARY OF INVENTION

According to a first aspect of the invention there is provided a microbial species described as *Lactobacillus plantarum/pentosus* and assigned the accession number PTA-1466 at the American Type Culture Collection (ATCC) (the strain being hereinafter referred to as the LPP strain).

The deposit referred to above was made at

American Type Culture Collection

10801 University Boulevard

Manassas

VA 201 10-2209

United States of America on Mar. 6, 2000.

According to a second aspect of the invention there is provided a method of preparing a shelf life enhancing composition for baking mixes which contain flour, the method comprising forming a starting mixture including flour and water and inoculating same with a culture of the LPP strain micro-organisms; allowing the mixture to ferment in order to produce anti-microbial substances including lactic acid, a peptide and possibly other presently unidentified anti-microbial substances; and terminating the fermentation process and destroying all living cells prior to the pH of the mix decreasing to 3.3 to yield a shelf life enhancing composition.

Further features of this aspect of the invention provide for the starting mixture to include glucose in order to expedite the fermentation process in which case the glucose is preferably present in an amount of about 1% m/v; for the fermentation to be carried out at a temperature of from 33 to 35° C.; for the fermentation to be terminated at a pH of about 3.4; for the fermentation process to be terminated by heat treating the mixture at a temperature of not more than 80° C. and preferably about 70° C.; and for the temperature of the product shelf life enhancing composition to be lowered to from 3 to 8° C. and preferably to about 4 or 5° C. for transport and storage purposes.

The invention also provides a shelf life enhancing composition produced by a method as defined above.

In order to produce a culture for use in the production of the shelf life enhancing composition defined above the LPP strain is inoculated into MRS (De Man Rogosa and Sharpe) broth (sold by Merck, Darmstadt, Germany) from colonies growing on MRS Agar (also sold by Merck) and incubated for a suitable period of time, generally from 48 to 72 hours at 30° C. without aeration.

In accordance with a third aspect of the invention there is provided a baking mix comprising a major amount of a bulk mixture including at least flour and water (which term includes milk for this purpose) and a minor amount of a shelf life enhancing composition as defined above.

The baking mix may, in particular, be a batter, and more particularly, but in no way exclusively, a muffin batter mix.

The proportion of the shelf life enhancing composition to the bulk mixture will depend on the objective to be achieved, the way in which the shelf life enhancing composition was prepared and the nature of the bulk mixture. In the case that the fermentation process was terminated at a pH of about 3.4, as a general rule, an amount of shelf life enhancing composition of about 14 to 16% (w/w) of the total baking mix will generally be effective.

It will however be appreciated by those skilled in the art, that individual situations will dictate their own optimal conditions both as to the manner in which the shelf life enhancing composition is prepared and in the proportions of that composition relative to the total baking mix that are to be used in order to achieve a desired objective and to provide a required degree of efficacy.

In order that the invention may be more fully understood one form of implementation thereof will now be described as well as the derivation of the particular strain of microbiological species forming the basis of the invention.

DETAILED DESCRIPTION OF THE INVENTION

The LLP Strain

The LPP strain was obtained from fermented sorghum grain. Samples taken from the latter were inoculated into MRS (Merck) broth and incubated at 30° C., without aeration for 2 to 3 days. The culture was streaked out onto MRS Agar (Merck) plates and incubated under the same conditions for a further 2 to 3 days. The colonies of the LLP strain were recovered from the plates and streaked out several times on MRS Agar (Merck) to obtain a pure culture. The strain has been deposited at the ATCC as indicated above.

Production of Cultures

Cultures of the LPP strain suitable for the production of shelf life enhancing compositions were produced by inoculating the LPP strain into 10ml MRS broth (Merck) from colonies growing on MRS Agar (Merck); incubating for 24 to 36 hours at 30° C. and subsequently inoculating the culture into 90 ml MRS broth (Merck). After another 24 hours of incubation at 30° C. the 100 ml of culture (approximately 100g) was ready to use in the preparation of a shelf life enhancing composition according to this invention.

Production of a Shelf Life Enhancing Composition

The shelf life enhancing composition is produced typically during the fermentation of cake flour which in the end will form a part of the flour content of a final baking mix. The shelf life enhancing composition produced in the manner described below can be stored, packaged and sold as such for subsequent addition to a baking mix by a customer for example, or it may be embodied in a baking mix immediately and the mix itself either being stored for later or progressive step-wise utilization or being packaged and sold as indicated below.

The shelf life enhancing composition is, as indicated above, produced by the fermentation of the flour which preferably takes place in the presence of about 1% (m/v) glucose. In order to produce the composition the cake flour, water and glucose are mixed together (called the fermentation mix) in proportions based on the ultimate quantity of baking mix required in a batch.

In the present case in which the composition is for use in a batter mix, for a final batter mix of about 100kg the fermentation mix will amount to about 14.61 kg made up as follows:

| | |
|---|---|
| Cake flour | 1,600 g |
| Glucose | 170 g |
| Culture | 840 g (more specifically, 840 ml) |
| Water | 12,000 g |

The fermentation was carried out for 13 hours at 33–35° C. with slow stirring and no aeration. Fermentation was continued until a final pH of approx. 3.4 was achieved after which stage the fermentation mix was heat-treated for 7 min at 70° C. in order to destroy all living microbial cells, including the LPP strain which will have produced the antimicrobial compounds in terms of this invention. As indicated above, these antimicrobial compounds include lactic acid, an antimicrobial peptide and, it is believed, one or more other antimicrobial compounds which have not been identified at the time of filing of this application. In any event, the antimicrobial compounds are highly effective as will be apparent from the following. This heat-treated fermentation mix forms the shelf life enhancing composition. It may be stored as such and may be packaged in suitable quantities for onward sale to customers either directly or indirectly by way of dealers. Storage should be at reduced temperature preferably about 4 to 60° C.

The Baking Mix

The shelf life enhancing composition, when required, may be used to produce a baking mix, in this case the muffin batter. In this case the shelf life enhancing composition constitutes about 14–16% (w/w) of the total mix which is made by adding the rest of the baking mix ingredients to the shelf life enhancing composition. In the example of a muffin batter for producing flavoured muffins the additional ingredients used were as follows:

| | |
|---|---|
| Cake Flour | 21,030 g |
| Water | 530 g |
| White sugar | 22,220 g |
| Emulsifier | 1210 g |
| Baking powder | 1210 g |
| Gum | 120 g |
| Gel | 650 g |
| Egg powder | 810 g |
| Fresh egg | 8080 g |
| Flavouring Additives | 5480 g |
| Sunflower oil | 24,250 g |

The Effect of the Compositions

The antimicrobial compounds formed in the shelf life enhancing composition have been found to be active against a number of food spoilage and pathogenic bacteria, including strains of Bacillus cereus, Clostridium sporogenes, Enterococcus faecalis, Listeria spp. and Staphylococcus spp.

The peptide is heat-stable at 80° C., but looses 50% of its activity after 60 min at 100° C. The peptide remains active after incubation at pH 2–9 and is inactivated when treated with pepsin, papain, alpha-chymotrypsin, trypsin and Proteinase K. The size of the peptide is estimated at 4 kDa, as determined by tricine-SDS-PAGE.

The mechanism of activity of the peptide is bactericidal.

Thus a batter intended for preservation according to the invention will preferably be prepared by introducing the shelf life enhancing composition containing the antimicrobial compounds to the other ingredients of the recipe. By mixing the shelf life enhancing composition with the rest of the batter ingredients in the proportions indicated, the antimicrobial compounds are present in the batter pre-mix at a concentration needed to be effectively antimicrobial.

In the case of a batter for muffins, a shelf life of at least four weeks was obtained with batter including the shelf life enhancing composition produced as described when stored at temperatures between 4° C. and 8° C.

To determine the effective concentration, i.e. the exact or minimum amount of the anti-microbial compounds needed in the batter to be anti-microbial or effectively bactericidal, requires taking into account a number of factors, e.g. the environment and resistance of the spoilage organisms in a specific batter. The type of cake flour used will also play a major role. The following experiments are illustrative.

Efficacy Experiments

Addition of the shelf life enhancing composition at a concentration of 0.5 μg (micrograms) per milliliter (ml) to mid-logarithmic growth phase (i.e. active growing) cells of Bacillus sp. decreased the number of viable Bacillus sp. cells from $2 \times 10^6$ to $1 \times 10^6$ cfu (colony forming units) per ml over a period of less than 24 hours. This experiment was done under strictly controlled conditions [i.e. at 37° C. in Nutrient Broth (Merck) medium, set at an initial pH of 7] and with a crude extract of the anti-microbial peptide only. The same experiment repeated with antimicrobial peptide which had been heated at 121° C. for 15 min (ie autoclaved) did not have the desired affect, i.e. cells of Bacillus were not killed.

The effect of the antimicrobial compounds produced by the LPP strain was evident in extending the shelf life of the batter described above. The batter, containing the shelf life enhancing composition, was examined by determining the presence of bacterial and yeast growth. The main problems typically encountered are the development of Bacillus species (which causes ropeyness), lactic acid bacteria and yeast.

The methods used were as follows: 10 g of the batter incorporating the shelf life enhancing composition were suspended into 90 ml of sterile distilled water (or 0.1% sterile peptone water) and homogenized for one minute. A dilution series was made in sterile distilled water (or 0.1% sterile peptone water) and 100 µl (micro-liters) plated onto Yeast Potato Dextrose (YPD) Agar and De Man Rogosa and Sharpe (MRS) Agar, respectively. The plates were incubated at 30° C. for two to three days and examined for yeast, mold and bacterial growth. This experiment was repeated every third day for up to six weeks on batter containing the shelf life enhancing composition which had been stored at 5° C. During this experiment the batter was stored in plastic sachets.

No bacterial, yeast or mold growth were detected for the first four weeks of storage. In week 5 a total microbial cell count of $1 \times 10^4$ per gram of batter were detected. By comparison, a control batter treated in the same way other than for the presence of the shelf life enhancing composition developed a total cell count of $1 \times 10^4$ per gram of batter after only 3 days of storage under the same conditions.

Extended experiments were conducted to show that the antimicrobial compounds produced by LPP strain do indeed extend the shelf life of the batter and without any drastic changes in the organoleptic characteristics of the pre-baked batter and quality of the baked product. For illustrative purposes, the muffin batter described above was used. It has to be noted that the shelf life enhancing composition forms part of the batter and is actually a pre-treatment of a portion of the batter, which is later mixed into the rest of the batter. No chemical preservatives are added at any stage of the production phase or thereafter.

The shelf life of the muffin batter was tested over a period of 63 days. The batter was kept in a cold room at 6–8° C. for the duration of the analysis. Extended studies were conducted, including microbiological. Controls were incorporated The microbiological tests conducted included total aerobic cell counts on PCA (Plate Count Agar, Merck), *Escherichia coli* counts on VRBD (Merck) plates and Salmonella counts on Salmonella-Shigella (Merck) plates. Ten grams of the ready-to-use batter, containing the shelf life extending antimicrobial compounds, was suspended into 100 ml of sterile 0.1% (m/v) peptone water, serially diluted and plated out onto the three different growth mediums mentioned. The plates were checked for the presence of colonies after 3–5 days of incubation at 30 and 37° C., respectively. These microbiological tests were conducted on days 3, 10, 12, 25, 32, 40, 52, 56 and 63 of storage at 6–8° C.

No microbial growth was detected in the ready-to-use batter for the first 4 weeks of storage on any of the three growth mediums. In week 5 a total microbial cell count of $1 \times 10^4$ per gram better was detected on PCA plates. The cell count gradually increased to $10^6$ cells per gram after 63 days of storage. No *E. coli* or Salmonella were detected on the respective growth media.

Ready-to-use batter that did not contain the shelf life enhancing composition showed signs of microbial spoilage within the first 4 days when stored under the same conditions. Total microbial cell counts of $1 \times 10^4$ were detected after 3 days of storage.

The pH, % moisture loss and levels of starch, sucrose and glucose in the batter including the shelf life enhancing composition did not show considerable changes during the first 4 weeks of storage in ready-to-use batter. Slight to more drastic changes of these characteristics were detected from day 40 to day 63 of storage.

The aroma profiles of baked muffins, produced from freshly prepared batter which contained the shelf life enhancing composition and from batter with the same shelf life enhancing composition, but which has been kept for several weeks (up to 40 days) and marked as also were determined.

The results obtained clearly indicated that the shelf life enhancing composition of this invention extended the shelf life of the batter to at least 4 weeks and in at least some cases up to 6 weeks, The aroma profiles of the baked muffins showed no major differences for any of five flavours tested over the 40-day test period. Furthermore, little differences were detected between muffins baked with freshly prepared batter and batter including the shelf life enhancing composition of 40 days old.

What is claimed is:

1. A microbial species described as *Lactobacillus plantarum/pentosus* and assigned the accession number PTA-1466 at the American Type Culture Collection (ATCC) (the strain being herein referred to as the LPP strain).

2. A method of preparing a shelf-life-enhancing composition for baking mixes which contain flour, the method comprising forming a starting mixture including flour and water and inoculating same with a culture of the microbial species *Lactobacillus plantarum/pentosus* of claim 1; fermenting the mixture in order to produce anti-microbial substances comprising lactic acid and an anti-microbial peptide; terminating the fermentation process and destroying all living cells prior to the pH of the mix decreasing to 3.3 to yield a shelf-life-enhancing composition.

3. A method as claimed in claim 2 in which the starting mixture includes glucose to expedite the fermentation process.

4. A method as claimed in claim 3 in which the glucose is present in an amount of about 1% m/v.

5. A method as claimed in claim 2 in which the fermentation is carried out at a temperature of from 33 to 35° C.

6. A method as claimed in claim 2 in which the fermentation is terminated at a pH of about 3.4.

7. A method as claimed in claim 2 in which the fermentation process is terminated by heat treating the mixture at a temperature of not more than 80° C.

8. A method as claimed in claim 7 in which the fermentation process is terminated by heat treating the mixture at a temperature of about 70° C.

9. A method as claimed in claim 2 in which the temperature of the product shelf-life-enhancing composition is lowered to from 3 to 8° C. for storage purposes subsequent to termination of the fermentation process.

10. A shelf-life-enhancing composition produced by a method as claimed in claim 2.

11. A baking mix comprising a major amount of a bulk mixture including at least flour and a minor amount of a shelf-life-enhancing composition as claimed in claim 10.

12. A baking mix as claimed in claim 11 in which the amount of shelf-life-enhancing composition constitutes about 14 to 16% (w/w) of the total baking mix.

13. A baking mix as claimed in claim 11 in which the baking mix is a batter.

14. A baking mix as claimed in claim 13 in which the baking mix is a muffin batter mix.

15. A method as claimed in claim 3 in which the fermentation is carried out at a temperature of from 33 to 35° C.

16. A method as claimed in claim 3 in which the fermentation is terminated at a pH of about 3.4.

17. A method as claimed in claim 3 in which the temperature of the product shelf life enhancing composition is lowered to from 3 to 8° C. for storage purposes subsequent to termination of the fermentation process.

18. A shelf-life-enhancing composition produced by a method as claimed in claim 3.

19. A shelf-life-enhancing composition produced by a method as claimed in claim 9.

20. A baking mix comprising a major amount of a bulk mixture including at least flour and a minor amount of a shelf-life-enhancing composition as claimed in claim 19.

* * * * *